United States Patent [19]

Mandoki

[11] Patent Number: 4,605,762

[45] Date of Patent: Aug. 12, 1986

[54] DEPOLYMERIZATION OF CONDENSATION POLYMERS

[75] Inventor: Jorge W. Mandoki, Cujimalpa, Mexico

[73] Assignee: Celanese Mexicana S.A., Mexico City, Mexico

[21] Appl. No.: 563,812

[22] Filed: Dec. 21, 1983

Related U.S. Application Data

[63] Continuation-in-part of Ser. No. 371,157, Apr. 23, 1982, abandoned.

[51] Int. Cl.$^4$ .................. C07C 51/487; C07C 27/02; C07C 85/26; C07D 487/00; C07D 210/00
[52] U.S. Cl. .................................. 562/483; 540/451; 540/538; 544/352; 562/485; 562/486; 562/593; 564/497; 564/498; 568/868; 568/871
[58] Field of Search ............... 562/483, 593, 486, 485; 564/497, 498; 568/868, 871; 544/352; 260/239.3 A

[56] References Cited

U.S. PATENT DOCUMENTS

| | | | |
|---|---|---|---|
| 2,793,235 | 5/1957 | Jenkinson | 562/483 X |
| 3,120,561 | 2/1964 | Chambret | 562/483 |
| 3,223,731 | 12/1965 | Craig | 562/483 |
| 3,952,053 | 4/1976 | Brown et al. | 562/483 |

FOREIGN PATENT DOCUMENTS

611032 12/1960 Canada.
49-76968 7/1974 Japan.

*Primary Examiner*—Natalie Trousof
*Assistant Examiner*—Vera C. Clarke
*Attorney, Agent, or Firm*—Forrest D. Stine

[57] ABSTRACT

A process for the neutral hydrolytic depolymerization of condensation polymers is described. The process is conducted in a continuous manner and comprises introducing condensation polymer waste material into an aqueous hydrolysis zone at a temperature of between 200° C. and 300° C. and superatmospheric pressure of at least 15 atmospheres. High pressure steam is introduced into the lower portion of the hydrolysis zone underneath the level of the condensation polymer waste material. The steam serves as the principal source of heat for the hydrolysis zone. By being introduced underneath the level of the condensation polymer waste material, the steam agitates the waste material to provide heat transfer to accelerate the hydrolysis reaction. Further, a portion of the steam condenses to provide water which is a reactant in the hydrolysis reaction. An aqueous solution of the product(s) of the hydrolysis reaction is withdrawn from an upper portion of the hydrolysis zone.

25 Claims, 1 Drawing Figure

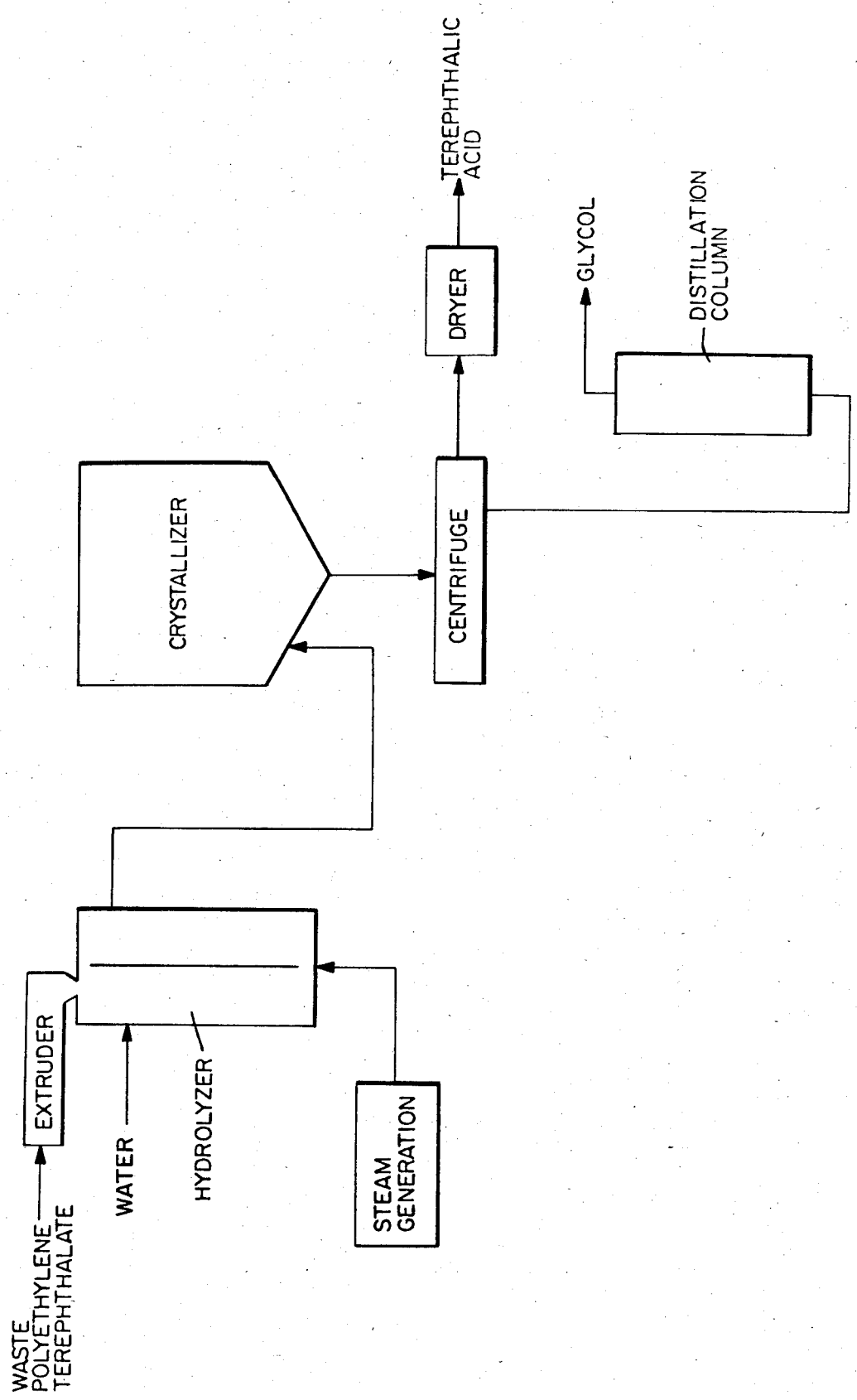

DEPOLYMERIZATION OF CONDENSATION POLYMERS

CROSS REFERENCE TO RELATED APPLICATION

This application is a continuation-in-part of my copending application Ser. No. 371,157, filed Apr. 23, 1982, now abandoned.

BACKGROUND OF THE INVENTION

This invention relates to a process for depolymerizing condensation polymers by hydrolysis. More particularly, this invention relates to the hydrolytic depolymerization of polyethylene terephthalate, polybutylene terephthalate, nylon 6 and nylon 66.

The neutral hydrolysis of polyethylene terephthalate at a high temperature and pressure is known in the art; see Ludewig, H. and Ramm, H.; German Economic Pat. No. 14,854 (1956); Littmann, E., "On the Preparation of Terephthalic Acid or its Dimethyl or Diglycol Ester from Polyethylene Terephthalate". Abh. d. Deutsch. Akad. d. Wiss. Kl. F. Chem., Geolog. Und Biochemie I (1963) pages 401–411; U.S. Pat. No. 3,120,561 to Chambret; and Japanese Kokai Pat. No. Sho. 49 [1974]-76968. "Neutral" hydrolysis is used herein to mean hydrolysis in which water is the only reactant other than the polyethylene terephthalate, i.e., no bases or acids are added.

SUMMARY OF THE INVENTION

A simple and economical process for the hydrolytic depolymerization of condensation polymers has now been found. The process is conducted in a continuous manner and comprises introducing condensation polymer waste material into an aqueous hydrolysis zone at a temperature of between 200° C. and 300° C. and superatmospheric pressure of at least 15 atmospheres. High pressure steam is introduced into the lower portion of the hydrolysis zone underneath the level of the condensation polymer waste material. The steam serves as the principal source of heat for the hydrolysis zone. By being introduced underneath the level of the condensation polymer waste material, the steam agitates the waste material to provide heat transfer to accelerate the hydrolysis reaction. Further, a portion of the steam condenses to provide water which is a reactant in the hydrolysis reaction. An aqueous solution of the product(s) of the hydrolysis reaction is withdrawn from an upper portion of the hydrolysis zone.

BRIEF DESCRIPTION OF THE DRAWING

The drawing illustrates a preferred apparatus arrangement for conducting the process of the invention with waste polyethylene terephthalate.

DETAILED DESCRIPTION OF THE INVENTION

Condensation polymer waste materials which may be hydrolyzed in accordance with the invention are well known in the art and do not per se constitute a part of this invention. Examples of condensation polymers include polyesters obtained by the condensation of a dicarboxylic acid and a dihydric alcohol and characterized by repeating units of the following formula:

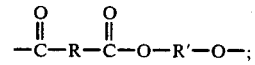

polyamides obtained by the condensation of a dicarboxylic acid and an alkylene diamine or by the head to tail condensation of an amino carboxylic acid or the corresponding lactam and characterized by the structural formulas:

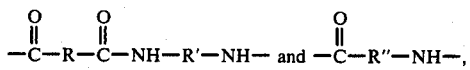

respectively; and polycarbonates obtained by the reaction of phosgene and a dihydric phenol and characterized by repeating units having the structure

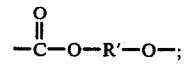

wherein R, R' and R" are divalent organic radicals. Specific condensation polymers which may be hydrolyzed in accordance with the invention include polyethylene terephthalate, polybutylene terephthalate, nylon 6 and nylon 66.

Condensation polymer waste materials which may be hydrolyzed in accordance with the invention may be waste material resulting from the manufacture of articles from the condensation polymers, e.g., waste material which is produced during the production of fibers, chip, film, molded articles such as bottles or the like. It may also take the form of low molecular weight oligomers produced during the manufacture of the condensation polymer. The polycondensation polymer waste material is supplied to the hydrolysis zone in the form of granules or yarns or in any other form suitable for handling, to the melting chamber of a screw-type extruder so that the extruder, in turn, feeds it in a continuous manner, to the hydrolyzer. Alternatively, the waste material can also be melted and injected continuously into the hydrolyzer by means of a high-pressure pump. Also, both can be used together, for example, in series.

In a simultaneous manner, water is injected or pumped into the hydrolyzer in a suitable proportion—that is, between 2-20 times the amount of the polymer. The water can be introduced cold or hot. Optionally, decolorizing carbon may be added in a proportion between 0.1% and 30%, based on the quantity of the treated waste, by feeding it into the hydrolyzer either with the polymer or suspended in water or introduced in bulk intermittently into the hydrolyzer. A filter aid, such as diatomaceous earth, may also be added.

The hydrolyzer utilized can be of any type, i.e., it can be cylindrical, vertical, horizontal, inclined, or it can be the U-shaped type, either vertical, horizontal or inclined. The hydrolyzer may be equipped with a source of heating which can be a jacket into which a heating fluid, liquid or vapor, is introduced, such as diphenyldiphenyl oxide or a hot oil or steam. The heating source can also be an interior or exterior coil, using one of the fluids previously mentioned. In the preferred embodiment of the invention, it will be understood that the principal source of heat is provided by means of high pressure steam introduced into the lower portion of the hydrolyzer underneath the level of the condensation polymer waste material. The steam agitates the condensation polymer waste material to provide heat transfer and to maximize contact between the waste material and the hot water in the hydrolyzer.

When the equipment is put into operation, the condensation polymer waste material which has not yet been hydrolyzed will be found in the lower part since it is more dense than water. If decolorizing carbon is utilized, it also will be in the lower part of the hydrolyzer. The supernatant liquid will be an aqueous solution of the products of the hydrolysis reaction, i.e., in the case of polyethylene terephthalate, it will be an aqueous solution of terephthalic acid and glycol. The supernatant is then further processed to recover the products of the hydrolysis reaction therefrom, e.g., by crystallization, distillation and/or evaporation of water.

The hydrolyzer is preferably operated at a water/polymer ratio of from 2 to 20. The quantity of water should be sufficient so as to keep the products of the hydrolysis reaction dissolved as they are being formed. Such a quantity will be dependent on the temperature at which the hydrolysis takes place. The hydrolysis temperature may vary between 200° C. and 300° C., preferably between 240° C. and 275° C. The greater the temperature, the higher will be the rate of the reaction, the higher will be the pressure in the equipment and the higher will be the solubility of products. The pressure in the hydrolyzer is preferably between 15 an 100 atmospheres. The pressure is a function of the temperature. The residence time of the material being hydrolyzed in the hydrolyzer is preferably from five minutes to six hours. The residence time required will depend on the temperature used and the morphology of the polymer. The indicated parameters are not independent of one another and upon modifying one of them, it may be necessary, or at least desirable, to change one or more of the others. It is preferred that the hydrolysis reaction be conducted in a neutral manner, i.e., in the absence of any reactant other than condensation polymer waste material and water, i.e., no bases or acids are added.

If decolorizing carbon is used, it is preferred to have a carbon/polymer ratio of 0.1% to 30% by weight. The quantity of carbon used will depend on the quantity of impurities in the polymer and the final purity desired in the products of the hydrolysis reaction produced.

The recovery of the hydrolysis products will now be more fully discussed by reference to the hydrolysis of waste polyethylene terephthalate in combination with decolorizing carbon. The supernatant liquid removed from the hydrolyzer will contain some proportion of the decolorizing carbon utilized, which will be suspended in the solution. This solution is subjected to a filtering operation under the temperature and pressure conditions in which the hydrolysis is carried out, with the object of eliminating the carbon and all the impurities absorbed by it. This filtration can be carried out in many diverse ways but the use of a heated cartridge filter is particularly preferred; this can be located outside or inside of the hydrolyzer—but preferably the filtration is undertaken by means of cartridges which are installed directly within the hydrolyzer.

Once the solution is filtered, the pressure to which it is subjected is released and it is sent to a continuous crystallizer which may be at atmospheric pressure, at a pressure higher than atmospheric pressure, or at a pressure lower than atmospheric pressure. The crystallizer can be continuous or batch with continuous preferred. In either case, one can use a single vessel or a plurality of vessels in series or parallel. This crystallizer can be equipped with a cooling jacket or a coil, or cooling may preferably be attained by simply venting the pressure. The residence time of the polyethylene terephthalate hydrolysis products in the crystallizer is preferably from five minutes to five hours. The residence time in the crystallizer will depend on the average size of the crystal desired, with the crystal being larger, the greater the residence time. The temperature in the crystallizer is preferably maintained at from −10° C. to 200° C.

The suspension of terephthalic acid obtained in this manner in the crystallizer is filtered continuously, either by using a filter or with a centrifuge. The crystals are washed in the same filtering device and are dried so as to be stored and recycled. The filtrate of the suspension, which is an aqueous glycol solution, is passed to distillation equipment where the glycol is obtained in pure form.

The following examples illustrate the invention:

EXAMPLE 1

In this embodiment, the method of the invention is carried out with the following equipment as illustrated in the drawing:
(a) A twin-screw melter extruder which is discharged by means of a multiple-orifice spray head, such as a spinneret, directly into the upper part of the hydrolyzer.
(b) A vertical cylindrical hydrolyzer which has a vertical plate in its interior which divides the hydrolyzer into two semicircular sections. Said plate does not have to extend along the whole length but rather will leave a free space both in the upper as well as the lower parts. The supply nozzle which is connected with the extruder is centered over one of the semicircles. On the upper part of the other semicircle there is a bundle of filter cartridges whose outlets are all connected with a common discharge tube. The entry of water is on one side of the hydrolyzer, the side corresponding to the supply of the polymer. The bottom of the hydrolyzer will be equipped with two connections—one which will be used for the introduction of live steam, and the drainage of said hydrolyzer being undertaken through the other connection.
(c) A continuous crystallizer which is made up of a vertical tank and a conical bottom, and which is equipped with venting means for release of pressure (not shown). The crystallizer is connected to the discharge tube of the filter cartridges (not shown) on the hydrolyzer by means of a line and an automatic valve which permits the passage of all the liquid in addition to a small quantity of steam which has an agitation function in the hydrolyzer. Said crystallizer also includes an automatic level control discharge device.
(d) A continuous centrifuge with a washing device which receives the discharge from the crystallizer and which, in turn, continuously discharges toward the drier.
(e) A drier of the fluidized bed type.
(f) A distillation column for the recovery of the glycol from the mother liquors from the centrifuge.

What has been described in the preceding is related to the equipment which is particularly preferred for carrying out the method, which consists of the following stages.

The hydrolyzer is loaded with a suitable quantity of water in a continuous manner by means of a metering pump. High-pressure saturated steam is also injected continuously into the lower part of the hydrolyzer. Waste polyethylene terephthalate, together with decolorizing carbon is fed continuously to the hydrolyzer by means of the extruder previously described.

The discharge from the hydrolyzer is adjusted in such a manner that it is slightly agitated by means of the excess steam.

Once the hydrolysis has been undertaken, the product is subjected to filtration in order to be subsequently crystallized. One should indicate that minimum agitation may be desirable in the crystallizer to keep the crystals suspended.

The crystals obtained are subjected to a drying stage, which is carried out in a drier which has the flow of air and the temperature suitably adjusted so that neither is excessive.

The distillation of the filtrate in turn, is carried out in the customary manner in order to obtain the glycol pure.

For the case particularly described, the specific reaction conditions are the following:

Water/polymer ratio—12,
Carbon/polymer ratio—10%,
Hydrolysis temperature—248° C.,
Hydrolysis pressure—42 atmospheres,
Residence time in the hydrolyzer—2 hours,
Frequency of carbon discharge every—24 hours,
Residence time in the crystallizer—4 hours,
Drying temperature—80° C.

EXAMPLE 2

When the process of Example 1 is repeated using as the feed material to the hydrolyzer polybutylene terephthalate waste material instead of the polyethylene terephthalate waste material used in Example 1, there are recovered terephthalic acid crystals, tetrahydrofuran and 1,4-butanediol. Tetrahydrofuran, which is the more thermodynamically stable thermal dehydration product of 1,4-butanediol greatly predominates. When vapors are continuously removed separately from the hydrolysis zone, essentially all the butanediol may be converted to tetrahydrofuran.

EXAMPLE 3

When the process of Example 1 is repeated substituting nylon 6 waste material for the polyethylene terephthalate waste material used in Example 1, caprolactam is recovered in roughly 80% of theoretical yield. The oligomers which are obtained during the hydrolysis reaction are recovered and recycled to the hydrolyzer.

EXAMPLE 4

When the process of Example 1 is repeated substituting nylon 66 waste material for the polyethylene terephthalate waste material of that example, there are produced as hydrolysis products hexamethylene diamine and adipic acid, which in water solution are present primarily as the salt of hexamethylene diamine with adipic acid. It is to be noted that hydrolysis of nylon 66 proceeds at a slower rate than hydrolysis of polyesters. Conversion efficiencies can be increased by increasing water to polymer ratio, increasing pressure or the like.

Although the invention has been described in considerable detail with particular reference to certain preferred embodiments thereof, variations and modifications can be effected within the spirit and scope of the invention as described hereinbefore, and as defined in the appended claims.

What is claimed is:

1. A continuous process for the hydrolytic depolymerization of condensation polymers which comprises:
    subjecting condensation polymer waste material selected from the group consisting of polyester polymer, polyamide polymer and polycarbonate polymer to aqueous hydrolysis in a hydrolysis zone at a temperature of between 200° C. and 300° C. and superatmospheric pressure of at least 15 atmospheres;
    introducing high pressure steam into the lower portion of the hydrolysis zone underneath the level of the condensation polymer waste material; and
    withdrawing an aqueous solution of the product(s) of the hydrolysis reaction from an upper portion of the hydrolysis zone.

2. A process as defined in claim 1 wherein said condensation polymer waste material is introduced into said hydrolysis zone by means of a screw extruder.

3. A process as defined in claim 2 wherein said aqueous hydrolysis is a neutral hydrolysis reaction.

4. A process as defined in claim 1 wherein said condensation polymer waste material is polyester waste material.

5. A process as defined in claim 4 wherein said polyester waste material is polyethylene terephthalate waste material.

6. A process as defined in claim 4 wherein said polyester waste material is polybutylene terephthalate waste material.

7. A process as defined in claim 1 wherein said condensation polymer waste material is polyamide waste material.

8. A process as defined in claim 7 wherein said polyamide is obtained by polycondensation of caprolactam.

9. A process as defined in claim 7 wherein said polyamide is obtained by the condensation of hexamethylenediamine with adipic acid.

10. A process as defined in claim 1 wherein said condensation polymer waste material is polycarbonate waste material.

11. A process as defined in claim 1 wherein said hydrolysis is conducted in the presence of decolorizing carbon in an amount of between 0.1–30 weight percent of said waste.

12. A process as defined in claim 1 wherein the quantity of water used in said hydrolysis step is sufficient to that required to keep the products of the hydrolysis reaction dissolved under the conditions of hydrolysis.

13. A process as defined in claim 1 wherein the time of the hydrolysis reaction is between 5 minutes and 6 hours.

14. A process as defined in claim 1 wherein said hydrolysis reaction is conducted at a temperature between 240° C. and 275° C.

15. A process as defined in claim 1 wherein the pressure in the hydrolysis zone is between 15 and 100 atmospheres.

16. The continuous process for obtaining pure terephthalic acid and glycol from polyethylene terephthalate waste comprising the steps:
    subjecting polyethylene terephthalate waste to neutral, aqueous hydrolysis in a hydrolysis zone at a temperature of between 200° C. and 300° C. and superatmospheric pressure of at least 15 atmospheres, said hydrolysis being conducted in the presence of decolorizing carbon in an amount of between 0.1 to 30 weight percent of said waste;

removing supernatant liquid from said hydrolysis zone and filtering said liquid under conditions of high temperature and pressure to recover an aqueous solution of terephthalic acid and glycol;

passing said aqueous solution of terephthalic acid and glycol to a crystallization zone and cooling said solution to a temperature of between −10° C. and 200° C. in said crystallization zone to thereby cause crystallization of terephthalic acid from said solution;

separating by filtering or centrifuge said terephthalic acid crystals from the liquid in said crystallization zone and washing and drying said crystals to provide pure terephthalic acid;

passing the liquid from said crystallization zone to a distillation zone and distilling said liquid to provide pure glycol.

17. The process defined in claim 16 wherein the quantity of water used in said hydrolysis step is greater than or equal to that required to keep the terephthalic acid dissolved under the conditions of hydrolysis.

18. The process defined in claim 17 wherein the time of the hydrolysis reaction is between 5 minutes and 6 hours.

19. The process defined in clam 16 wherein said cooling in said crystallization zone is accomplished by venting the pressure in the crystallizer.

20. The process defined in claim 19 wherein the final pressure in the crystallization zone is equal to atmospheric pressure.

21. The process defined in claim 19 wherein the final pressure in the crystallization zone is between 1 mm Hg. absolute and atmospheric pressure.

22. The process defined in claim 19 wherein the final pressure in the crystallization zone is between atmospheric pressure and 15 atmospheres.

23. The process defined in claim 16 wherein said cooling in said crystallization zone is accomplished by means of heat exchange with a cold surface.

24. The process of claim 16 wherein said cooling in said crystallization zone is accomplished by both heat exchange with a cold surface and a simultaneous venting of pressure.

25. The process defined in claim 16 wherein said aqueous solution of terephthalic acid in glycol is maintained in said crystallization zone for a time of between about 5 minutes and 5 hours.

* * * * *